United States Patent
Gooberman

(12) 
(10) Patent No.: US 11,351,128 B1
(45) Date of Patent: *Jun. 7, 2022

(54) PHARMACEUTICAL COMPOSITIONS AND METHODS OF ADMINISTRATION

(71) Applicant: Lance L. Gooberman, Merchantville, NJ (US)

(72) Inventor: Lance L. Gooberman, Merchantville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/319,595

(22) Filed: May 13, 2021

(51) Int. Cl.
*A61K 31/145* (2006.01)
*A61K 9/00* (2006.01)
*A61K 45/06* (2006.01)
*A61K 47/10* (2017.01)
*A61K 47/38* (2006.01)

(52) U.S. Cl.
CPC .......... *A61K 31/145* (2013.01); *A61K 9/0019* (2013.01); *A61K 45/06* (2013.01); *A61K 47/10* (2013.01); *A61K 47/38* (2013.01)

(58) Field of Classification Search
CPC .................................................. A61K 31/145
See application file for complete search history.

(56) References Cited

U.S. PATENT DOCUMENTS

| 6,589,987 B2 * | 7/2003 | Kennedy ........ C12Y 116/03001 514/491 |
| 8,791,093 B2 * | 7/2014 | Gooberman ......... A61K 31/439 514/171 |
| 2019/0117630 A1 * | 4/2019 | Rajakas ............... A61K 31/704 |

OTHER PUBLICATIONS

Tyring et al. CAS: 92: 105587, 1979.*

* cited by examiner

*Primary Examiner* — Rei Tsang Shiao
(74) *Attorney, Agent, or Firm* — John P. Luther

(57) ABSTRACT

Provided is a pharmaceutical composition for injection into a host in need thereof comprising an extended release diluent suspension of disulfiram, and optionally comprising steroidal anti-inflammatory agent.

9 Claims, No Drawings

PHARMACEUTICAL COMPOSITIONS AND METHODS OF ADMINISTRATION

FIELD OF THE INVENTION

The present invention provides a pharmaceutical composition for injection into a host in need thereof comprising an extended release diluent suspension of disulfiram, and optionally comprising a steroidal anti-inflammatory agent.

BACKGROUND ART

Substance addiction typically follows a course of tolerance, withdrawal, compulsive drug taking behavior, drug seeking behavior, and relapse. Addictive substances include alcohol, caffeine, nicotine, cannabis and cannabis derivatives, opiates and other morphine-like opioid agonists such as heroin, phencyclidine and phencyclidine-like compounds, sedative hypnotics such as benzodiazepines and barbiturates and psychostimulants, such as cocaine, amphetamines and amphetamine-related drugs such as dextroamphetamine and methylamphetamine. Substance abuse and addiction are public health issues. They have significant social and economic impact on both the addict and society by playing a major role in violent crime and the spread of infectious diseases. Amongst all these substance addictions, alcohol and stimulants addiction is one of the most concerned problem addition issues today in the U.S.

As certainly well known, alcohol abuse and dependency has been a long standing problem throughout the world and throughout the ages. Notwithstanding, in treating alcohol abuse and dependency there have been limited pharmacological approaches available. For many years, medications essentially were limited to use of Antabuse, the brand name for Disulfiram, starting in 1951. Antabuse is an orally administered tablet which works as a deterrent to alcohol use by producing negative systems in a person when they consume alcohol.

As orally administered compliance issues are associated with Antabuse, especially considering its negative effects when taken with alcohol, non-motivated or otherwise alcohol addicted people stop taking their tablets so that they might resume drinking alcohol as soon as adverse effects wear off.

Acamprosate sold under the brand name Campral is also a medication used along with counseling to treat alcohol dependence. Acamprosate is thought to stabilize chemical signaling in the brain that would otherwise be disrupted by alcohol withdrawal. When used alone, acamprosate is not an effective therapy for alcoholism in many or most individuals. It only works best when used with psychological support, which also presents a serious compliance problem. The drug also produces sometimes serious side effects, including allergic reactions, low or high blood pressure, with diarrhea the most common side effect. People with kidney problems have also been advised to not take the drug.

Sometime in the early 1990s the use of Vivitrol, a long-acting or otherwise extended release suspension form of Naltrexone, became approved by the FDA in the treatment of alcohol abuse. Vivitrol is typically a once monthly intramuscular injection that works to treat alcohol abuse by blocking the euphoric and sedative effects of drinking alcohol. The issues of compliance are thus greatly reduced.

By blocking the euphoric and sedative effects of drinking alcohol, Vivitrol works to reverse the conditioned responses to the pleasurable effects of alcohol. The therapy is indicated for those who are not in complete abstinence. Thus, for those who are only interested in abstinence from day one of a rehabilitation program, Vivitrol is not the correct choice since the possibility of complete deconditioning does not exist.

Additionally, oftentimes a person is also fighting both opioid and alcohol abuse and addiction. While Vivitrol is also used to prevent relapse to opioid dependence, and to also treat opioid overdose or more importantly synthetic opioid overdose, such as fentanyl and fentanyl analogs, Vivitrol may interact with various antagonists, such as buprenorphine and naltrexone. Alternatively, Vivitrol may also interact with intended narcotic pain medications, which are needed when nothing else will do, such as, for example, butorphanol, codeine, hydrocodone, hydromorphone, levorphanol, mederidine, methadone, morphine, nalbuphine, oxycodone, oxymorphone, or propoxyphene.

It is also possible to experience withdrawal symptoms when treated with Vivitrol, if there are traces of opioid recovery medications present. Some serious side effects can include hallucinations, confusion, blurred vision and severe vomiting, anxiety and diarrhea.

There therefore exists a need for a long term-type injectable formulation for disulfiram for those interested in the possibility of complete alcohol abstinence for the long term, and perhaps for life, and which avoids the possible deleterious effects of Vivitrol.

DETAILED DISCUSSION OF PREFERRED EMBODIMENTS

Disulfiram (tetraethyldisulfane-carbothioamide or 1-(diethylthiocarbamoyl-disulfanyl)-N,N-diethyl-methanethioamide) sold under the trade name or mark Antabuse is a drug traditionally used to support the treatment of alcoholism. The drug produces an acute sensitivity to ethanol consumption by inhibiting the enzyme acetaldehyde dehydrogenase causing, inter alia, even in small amounts with alcohol, flushing, throbbing headache, nausea, respiratory difficulty, oftentimes violent vomiting, sweating, perspiration, hyperventilation, increased heart rate, and sometimes heart attack, unconsciousness and death. Inhibition of acetaldehyde dehydrogenase enables concentration of acetaldehyde to build up causing the aforesaid symptoms which are sometimes those associated with severe hangover symptoms.

Disulfiram should not be taken if alcohol has been consumed in the previous 12 hours or so to avoid the effects discussed above. There is no tolerance to disulfiram, and the longer it is taken the stronger its effects, which is one of the reasons it is chosen for or by those who desire total alcohol abstinence and thus ideal candidates are those who have completed alcohol withdrawal and are committed to abstinence. As disulfiram is absorbed slowly through the body's digestive tract and eliminated slowly by the body, its effects may last up to two weeks after initial intake depending on dosage. Typical oral tablet dosages are about 250 to about 500 mg per day on a daily basis.

Disulfiram, however, is not known to reduce alcohol cravings, outside of the known severe discomfort of the consequences of consuming alcohol in its presence. Therefore, a major problem associated with disulphiram is extremely poor compliance. Methods to improve compliance have included sub-dermal implants which release the drug continuously over time, such as a period of up to 12 weeks, and supervised administration practices, for example, having the drug regularly administered by one's peer or spouse. The former has shown problems with infection and/or body rejections, and the later more compliance problems. The inventive injectable extended release disulfiram comprising compositions avoid these problems.

Disulfiram has also shown efficacy in various other treatment indications, and for which its use is contemplated herein. One of the important uses is for treatment of COVID-19 infections, and as a possible prophylactic treatment to prevent COVID-19 infection over an extendable release time period. See, for example, Tamburin et al., InterSERT di Collaborazione Scientifica (GICS) (2021) "COVID-19 and related symptoms in patients under disulfiram for alcohol use disorder" study of efficacy on COVID-19 symptoms. Any anti-viral, e.g. anti-Covid, efficacious effective amount of disulfiram for use in the inventive injectables is thought suitable herein, or at least any amount that is efficacious in reducing viral load.

Disulfiram has also shown efficacy in treatment of stimulant use disorders, such as cocaine and methamphetamine, which have presented significant public health problems, and for which use is also contemplated herein. See, e.g., UAMA New Release, Mar. 2, 2004 "Disulfiram Reduces Cocaine Use In Study." The use of disulfiram in the inventive injectables for such treatment is in any efficacious anti-stimulant effective amount to inhibit or reduce cravings and/or to inhibit or reduce stimulant effects.

Disulfiram a multi-enzyme inhibitor also exhibits anti-cancer properties, such as, for example against melanoma and use in general as antineoplastic medication. See, e.g., Meraz-Torres et al., Cancers 2020, 12, 3538, "Disulfiram as a Therapeutic Agent for Metastatic Malignant Melanoma-Old Myth or New Logos?" and Nechushtan et al., Department of Oncology, Hadassah-Hebrew University Medical Center Israel (2018) "There must be another way-disulfiram and cancer treatment: Editorial on alcohol-abuse drug disulfiram targets cancer via p97 segregase adaptor NPL4." With the current cost of new anticancer therapies being what only can be described as astronomical, and that of even older drugs being out of reach for many, the repurpose of an older known drug for which there is ample safety information is an attractive and perhaps lifesaving alternative. See also e.g., Wu et al., Scientific Reports Article No.: 256 (2019), "Disulfiram and BKM 120 in combination with chemotherapy impede tumor progression and delay tumor recurrence in tumor indicating cell-rich THCB." Thus, the disulfiram injectable suspensions of the invention are contemplated for use in treating cancers or tumors with disulfiram being present in any efficacious therapeutic antineoplastic amount alone or in combination with other antineoplastic pharmaceuticals, such as, for instance, taxol (paclitaxel) and doxorubicin in breast cancer treatment and in treatment for melanomas.

Disulfiram has also found use in treatment of lyme disease and babesiosis and is considered a breakthrough in treatment of these diseases. Dosage has been suggested in the range of from about 62 mg to about 125 mg every three days or so, but increasing as needed to eradicate any effects of these diseases. In reality, any efficacious effective anti-lyme disease or anti-babesiosis is contemplated for use in the inventive disulfiram injectables. See, for example: Scheibel L W, Adler A, Trager W. Tetraethylthiuram disulfide (Antabuse) inhibits the human malaria parasite *Plasmodium falciparum. Proc Natl Acad Sci U.S.A.* 1979; 76(10):5303-7; Pothineni V R, Wagh D, Babar M M, et al. Identification of new drug candidates against *Borrelia burgdorferi* using high-throughput screening. *Drug Des Devel Ther.* 2016:10:1307-22; Liegner K B. Disulfiram (Tetraethylthiuram Disulfide) in the Treatment of Lyme Disease and Babesiosis: Report of Experience in Three Cases. Antibiotics (Basel). 2019 May 30; 8(2). Pii: E72. doi:10.3390/antibiotics8020072.

A drug repurposing strategy has also identified anti-obesity effects of disulfiram and for which efficacy is also contemplated for use with the disulfiram injectables of the invention. See Omron et al., Diabetes Metabolic Syndrome and Obesity, 2020:13, 1473-1480.

In view of the above, a first aspect of the invention is directed to an injectable extended release composition comprising disulfiram for treatment of alcohol consumption disorders, and which avoids problems with administration compliance to maintain long term alcohol consumption abstinence as desired.

Disulfiram is a white, odorless essentially tasteless powder somewhat soluble in water to the extent of about 20 mg in 100 ml. Taking advantage of such limited solubility, the injectable compositions of the invention for alcohol-abuse treatment, and other treatments as described, comprise disulfiram in amounts of from about 50 mg up to 800 mg in ml water (carrier suspension) vehicle sufficient to form a slurry or suspension, and optionally other agents or ingredients such as to form a slow or extended release slurry or suspension, or in any amount found to provide an injectable suspension. Injectable compositions of the invention may also comprise the following non-limiting ingredients which have shown extended release for a month or more such as, of course, sufficient water to make up an injectable disulfiram suspension of the contemplated slow release dosage, isotonicity agents, such as sodium chloride, preservatives, such as benzyl alcohol, thickeners and/or emulsifiers or suspension agents, such as carboxymethylcellulose, and polysorbate 20 or 80, and pH adjusters, such as acid (HCL) and sodium hydroxide.

The volume of water, or carrier suspension vehicle, may generally range from about 2 ml up to 100 ml, but is not critical to the invention as any amount can be made up for later portions to be used in injection devices such as the syringes and the like.

Polymers, such as employed in subcutaneous implantable formulations, e.g. biodegradable polymers, such as Poly Lactic-co-Glycolic Acid (PLGA), are not desired nor needed as such tend to clog injection devices, such as needles.

pH is ideally preferred to be somewhere around 5.0 to 7.5. Ampoules prepared for injection may also have air inside replaced with nitrogen to retard oxidation.

Additionally, a steroidal anti-inflammatory agent may be added to the diluent in injectable composition preparation to aid in extending delayed delivery times. Such may include, for example, triamcinolone acetonide.

Example 1: Optional Preparation for Alcohol-Abuse Treatment

A diluent solution is prepared using the desired ml of sterile water for the contemplated disulfiram concentration of about 200 mg to 800 mg. Sufficient water is used to ensure a disulfiram suspension in water that is flowable and injectable. Sodium chloride is added for the desired isotonicity along with 0.99% (w/v) benzyl alcohol as a preservative and 25-50 mg carboxymethyl-cellulose sodium, polysorbate 20 or 80 from 0.05 to 30 plus mg may also be added. Preferably the disulfiram is sifted to avoid crumping prior to mixing with the clear prepared diluent solution. pH is adjusted as desired, or appropriate.

Triamcinolone acetamide may optionally added to the diluent preparation in any amount deemed desired for extended duration of injected disulfiram, but usually in amounts of from about 10 to 120 mg, and in some embodiments from about 20 mg to about 80 mg, and in other embodiments from about 30 mg to about 60 mg depending upon total volume.

Example 2: Preparation for Alcohol-Abuse Treatment

Optionally, from about 200 to about 500 mg disulfiram is added to a sufficient amount of sterile water to form a slurry or aqueous suspension of the desired thickness, wherein each ml of the aqueous suspension comprises 40 mg triamcinolone acetonide with sodium chloride for isotonicity, 0.99% (w/v) benzyl alcohol as a preservative, 0.75% carboxymethylcellulose sodium and 0.04% polysorbate 80 with sodium hydroxide or hydrochloric acid present to adjust pH to 3.0 to 7.5.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. An extended release disulfiram injectable composition comprising from 50 mg to 800 mg disulfiram and water sufficient for suspension of the disulfiram, carboxymethylcellulose sodium of from about 25 mg to about 50 mg, and having a pH of from 5.0 to 7.5.

2. The composition of claim 1 further comprising polysorbate 20 or 80 of from about 0.05 mg to about 30 mg, an isotonicity agent and optionally a preservative.

3. The composition of claim 1 further comprising a steroidal anti-inflammatory agent.

4. The composition of claim 1 comprising from about 200 to about 800 mg disulfiram useful for treating alcohol-abuse in humans.

5. The composition of claim 1 useful for treating viral infections in humans.

6. The composition of claim 5 wherein the viral infection is COVID.

7. The composition of claim 1 useful for treating stimulant abuse in humans.

8. The composition of claim 1 useful as antineoplastic agent in humans.

9. The composition of claim 1 useful for treating Lyme disease in humans.

* * * * *